(12) United States Patent
Kortenbach et al.

(10) Patent No.: US 6,808,491 B2
(45) Date of Patent: Oct. 26, 2004

(54) METHODS AND APPARATUS FOR ON-ENDOSCOPE INSTRUMENTS HAVING END EFFECTORS AND COMBINATIONS OF ON-ENDOSCOPE AND THROUGH-ENDOSCOPE INSTRUMENTS

(75) Inventors: Juergen A. Kortenbach, Miami Springs, FL (US); Michael Sean McBrayer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 10/151,503

(22) Filed: May 20, 2002

(65) Prior Publication Data

US 2002/0173786 A1 Nov. 21, 2002

Related U.S. Application Data

(60) Provisional application No. 60/292,419, filed on May 21, 2001.

(51) Int. Cl.[7] .............................................. A61B 1/018
(52) U.S. Cl. ...................... 600/104; 600/106; 600/153; 600/127
(58) Field of Search ................... 600/104, 106, 600/153, 105, 127; 606/139, 205, 51, 142

(56) References Cited

U.S. PATENT DOCUMENTS

| | | | | |
|---|---|---|---|---|
| 4,027,510 A | * | 6/1977 | Hiltebrandt ..................... 72/37 |
| 4,330,564 A | * | 5/1982 | Friedman ..................... 426/417 |
| 4,444,462 A | * | 4/1984 | Ono et al. ..................... 385/119 |
| 4,538,594 A | * | 9/1985 | Boebel et al. ............... 600/102 |
| 4,759,348 A | * | 7/1988 | Cawood ....................... 600/102 |
| 5,131,379 A | * | 7/1992 | Sewell, Jr. .................... 600/104 |
| 5,336,222 A | | 8/1994 | Durgin, Jr. et al. ........... 606/50 |
| 5,389,098 A | * | 2/1995 | Tsuruta et al. ................ 606/41 |
| 5,389,104 A | | 2/1995 | Hahnen et al. .............. 606/174 |
| 5,395,369 A | | 3/1995 | McBrayer et al. ............ 606/51 |
| 5,496,310 A | | 3/1996 | Exconde et al. ............. 606/205 |
| 5,503,616 A | * | 4/1996 | Jones ........................... 600/153 |
| 5,507,797 A | | 4/1996 | Suzuki et al. ................ 606/140 |
| 5,582,617 A | | 12/1996 | Klieman et al. ............. 606/170 |
| 5,667,473 A | * | 9/1997 | Finn et al. ................... 600/104 |
| 5,707,344 A | | 1/1998 | Nakazawa et al. .......... 600/127 |
| 5,755,726 A | * | 5/1998 | Pratt et al. ................... 606/143 |
| 5,814,054 A | | 9/1998 | Kortenbach et al. ......... 606/139 |
| 5,817,013 A | * | 10/1998 | Ginn et al. .................. 600/114 |
| 5,820,630 A | | 10/1998 | Lind ........................... 606/208 |
| 5,857,961 A | * | 1/1999 | Vanden Hoek et al. ..... 600/104 |
| 5,951,545 A | | 9/1999 | Schilling et al. .............. 606/37 |
| 5,968,056 A | | 10/1999 | Chu et al. .................... 606/140 |
| 6,001,110 A | | 12/1999 | Adams ........................ 606/151 |
| 6,071,233 A | * | 6/2000 | Ishikawa et al. ............. 600/104 |
| 6,086,528 A | * | 7/2000 | Adair ........................... 600/104 |
| 6,110,127 A | | 8/2000 | Suzuki ......................... 600/565 |
| 6,119,913 A | | 9/2000 | Adams et al. ............ 227/176.1 |
| 6,221,007 B1 | * | 4/2001 | Green .......................... 600/160 |
| 6,277,064 B1 | * | 8/2001 | Yoon ........................... 600/114 |
| 6,352,503 B1 | * | 3/2002 | Matsui et al. ................ 600/104 |
| 6,464,685 B1 | * | 10/2002 | Suzuki et al. ............... 604/534 |
| 6,527,753 B2 | * | 3/2003 | Sekine et al. ................ 604/264 |
| 2001/0049509 A1 | * | 12/2001 | Sekine et al. ................ 604/264 |

* cited by examiner

*Primary Examiner*—John P. Leubecker
(74) *Attorney, Agent, or Firm*—Gordon & Jacobson, PC (57) ABSTRACT

A surgical system includes an endoscope, a pair of end effectors provided on the outside of the distal end of a endoscope ("on-scope"), in which one end effector is rotatable or otherwise movable relative to the second end effector and in which such movement is effected via controls elements which do not extend through a lumen of the endoscope, and another instrument extending through the lumen of the endoscope ("through-scope"), and which preferably also has a pair of end effectors. The on-scope device may be clamping jaws, needle passers, clip appliers, cautery devices, staplers, and releasable hemoclips, among other end devices. The through-scope end effectors may be graspers and clip appliers, among other end effectors.

15 Claims, 10 Drawing Sheets

METHODS AND APPARATUS FOR ON-ENDOSCOPE INSTRUMENTS HAVING END EFFECTORS AND COMBINATIONS OF ON-ENDOSCOPE AND THROUGH-ENDOSCOPE INSTRUMENTS

This application claims priority from U.S. Provisional Application No. 60/292,419, filed May 21, 2001, and U.S. Ser. No. 09/730,911, filed Dec. 6, 2000, which are hereby incorporated by reference herein in their entireties.

BACKGROUND OF THE INVENTION

1. Field of the Invention

The invention relates to surgical instruments and methods. More particularly, the invention relates to methods and apparatus for the minimally invasive procedures in which an endoscope is used.

2. State of the Art

Minimally invasive (also known as endoscopic) surgery is not a new technology. However, it is only in recent years that such surgery has become so widely accepted that it is used in many diverse procedures. Minimally invasive surgery typically involves the making of a small incision (5–10 mm) in the vicinity of the surgical site, the installation of a port through the incision, and the extension of an endoscope through the port to the surgical site. Alternatively, an endoscope is sometimes lubricated and inserted through a body cavity such as the rectum or esophagus.

Gastrointestinal bleeding is a somewhat common and serious condition that can be fatal if left untreated. This problem has prompted the development of a number of endoscopic therapeutic approaches to achieve hemostasis, such as the injection of sclerosing agents, the attachment of mechanical hemostatic devices and contact electrocautery techniques. Mechanical hemostatic devices are typically in the form of clamps, clips, staples, sutures, etc. which are able to apply sufficient constrictive forces to blood vessels so as to limit or interrupt blood flow. Such devices are disclosed in U.S. Pat. No. 6,001,110. Electrocautery techniques involve the use of either monopolar or bipolar electrodes which are contacted to ulcerous tissue. A well known electrocautery device is disclosed in U.S. Pat. No. 5,336,222.

The known clip techniques and cautery techniques are only adequate for relatively small ulcers because the clips and/or cautery probes must be delivered through the working lumen of an endoscope. In addition to optical elements which carry fiber optics to illuminate the surgical site and which deliver an image from the surgical site, the endoscope typically has two or three lumina: one or two lumen (a) for aspiration and irrigation, and one (the working lumen) through which a surgical tool may be passed. The working lumen is typically very small in size (e.g., about 3 mm in diameter), and thus the size of the tools which may be used with a typical endoscope are severely limited in size.

Bleeding gastric ulcer lesions are not limited in size and are frequently too large to be effectively treated with the known mechanical and electrical techniques.

SUMMARY OF THE INVENTION

It is therefore an object of the invention to provide methods and apparatus for the minimally invasive treatment of gastric ulcers.

It is also an object of the invention to provide methods and apparatus for the minimally invasive treatment of gastric ulcers using a cautery device.

It is another object of the invention to provide methods and apparatus for the minimally invasive treatment of gastric ulcers using a cautery device which is capable of treating relatively large lesions.

It is a further object of the invention to provide methods and apparatus for the minimally invasive treatment of gastric ulcers using a cautery device which is usable in conjunction with existing endoscopes.

In accord with these objects which will be discussed in detail below, the apparatus of the present invention includes a flexible coil having a proximal end and a distal end (as used herein proximal end means the end closest to the practitioner and distal end means the end closest to the surgical site) with a pull wire extending therethrough. An actuation device is coupled to the proximal ends of the coil and the pull wire for reciprocally moving one of the pull wire and the coil relative to the other. A pair of jaws are coupled to the distal ends of the coil and pull wire such that relative movement of the coil and pull wire causes opening and closing of the jaws. The jaws are rotatably coupled to a clevis means which is adapted to be coupled to the distal end of an endoscope. According to the invention, at least one jaw has an "open" structure, with a rim but substantially no jaw cup. The jaws are U-shaped, semi-circular, or horse shoe shaped and are provided with a cautery capability by selectively coupling the coil, the pull wire, or both to a source of cauterizing energy.

According to one of the methods of the invention, the clevis is attached to the distal end of an endoscope and the distal end of the endoscope is delivered to the surgical site with the aid of the optics of the endoscope and with the jaws of the invention closed by activation of the actuation device. A grasper (used herein to denote any instrument such as a forceps, biopsy forceps, snare, suction device or other instrument for mechanically or otherwise grabbing, gripping, or retaining tissue) is inserted through the working lumen of the endoscope. The jaws of the apparatus of the invention are then opened so that the grasper is extended between the opened jaws (typically through the open structure of at least one jaw) to grasp the ulcerous tissue. The grasping instrument is withdrawn to pull the ulcerous tissue between the opened jaws. When the tissue is in place, the jaws of the present invention are closed and the cauterizing energy is activated to cauterize the ulcerous tissue and thereby result in hemostasis. The procedure may be repeated for treatment of other ulcerous tissue in the vicinity before the apparatus is withdrawn with the endoscope.

According to the presently preferred embodiment, one of the jaws of the cautery device is coupled to the coil and the other is coupled to the pull wire, whereas both jaws are coupled to the clevis. This arrangement permits the jaws to assume two different closed positions: a first closed position wherein both jaws extend substantially parallel and adjacent to the face of the distal end of the endoscope and a second closed position where both jaws extend substantially perpendicular to the face of the distal end of the endoscope. The first closed position is preferred when moving the endoscope to and from the surgical site, and because the jaws have an open structure, the jaws do not block the optical "vision" of the endoscope.

According to a further preferred aspect of the invention, the clevis is provided with upper and lower stops and the coil and pull wire are coupled to the jaws in such a way that different moment arms result. This permits the jaws to be moved from the first closed position to an open position, to the second closed position, and back to the first closed position with a single actuation device having a single linear movement.

According to still another preferred aspect of the invention, the jaws are insulated from each other at their pivotal connection to the clevis so that they may be provided with bipolar cautery capability via separate connections to the coil and pull wire which are also insulated from each other.

According to other embodiments of the invention, various examples are provided embodying the broad concept of having a pair of end effectors on the outside of the distal end of the endoscope ("on-scope"), in which one end effector is rotatable or otherwise movable relative to the second end effector, and also having another instrument extending through the lumen of the endoscope ("through-scope"), particularly where such other instrument also has a pair of end effectors. By way of example, and not by limitation, the described "on-scope" end effectors include clamping jaws, needle passers, clip appliers, cautery devices, staplers, and releasable hemoclips. By way of example, and not by limitation, the described "through-scope" end effectors include graspers and clip appliers.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
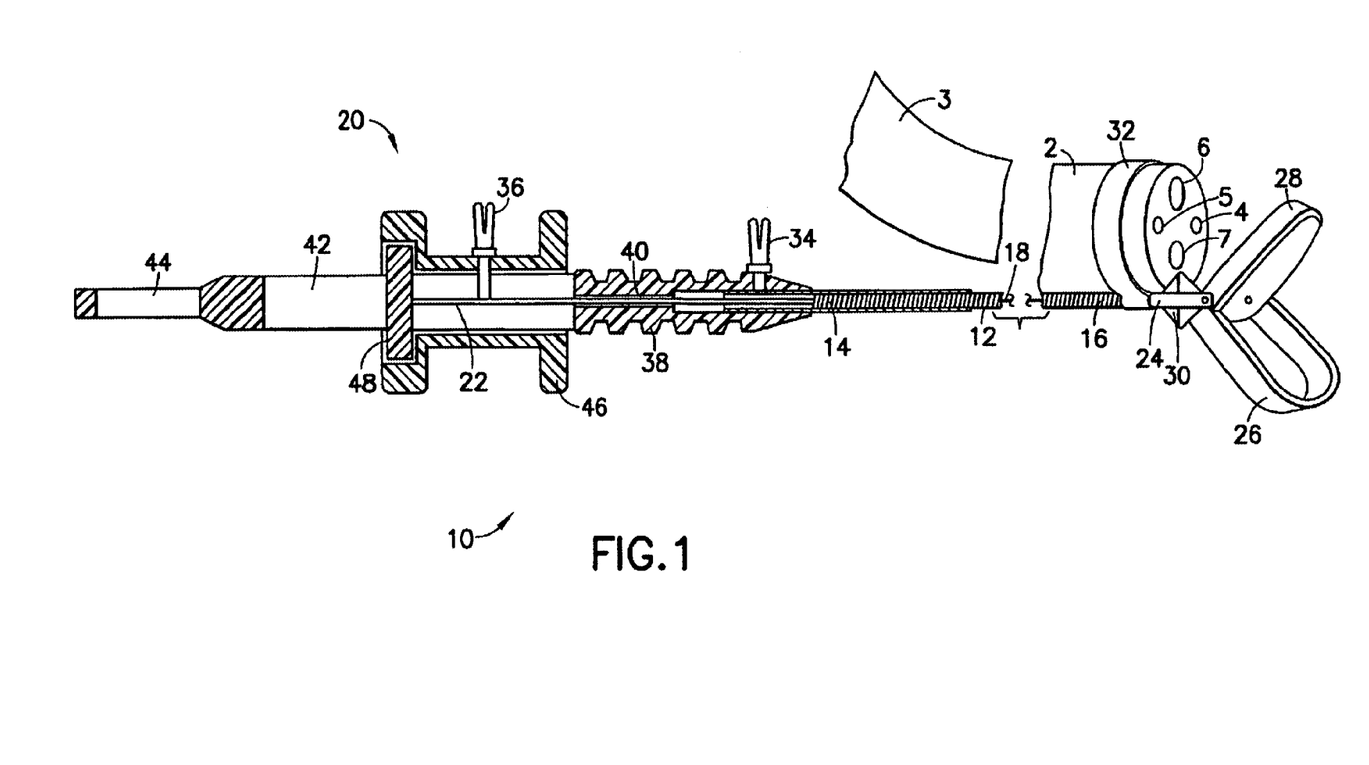
FIG. 1 is a schematic broken side elevation view in partial section and partial perspective of a first embodiment of the apparatus of the invention.

Turning now to FIG. 1, an apparatus 10 according to a first embodiment of the invention includes a flexible coil 12 having a proximal end 14 and a distal end 16 with a pull wire 18 extending therethrough. An actuation device 20, described in more detail below, is coupled to the proximal end 14 of the coil and the proximal end 22 of the pull wire for reciprocally moving one of the pull wire and the coil relative to the other. A clevis 24 is coupled to the distal end 16 of the coil 12 and a pair of jaws 26, 28 are rotatably coupled to the clevis. The jaws 26, 28 are also coupled to the distal end 30 of the pull wire 18 such that movement of one of the pull wire or the coil relative to the other causes the jaws to open or close. According to one aspect of the invention, the clevis 24 is provided with an upstanding ring 32 which is adapted to attach to the distal end 2 of a conventional endoscope 3 having optical elements 4 and 5 which carry fiber optics for illumination and a lens and fiber optics for capturing an image, an irrigation/aspiration lumen 6, and a lumen 7 which constitutes a hollow working channel for receiving an instrument. According to another aspect of the invention, the jaws 26, 28 are substantially larger than the working channel 7 so as to be able to cauterize relatively large ulcers. According to yet another aspect of the invention, the jaws are coupled to the endoscope such that they rotate about an axis transverse to the longitudinal axis of the endoscope; i.e., the axis of rotation is obliquely angled relative to the longitudinal axis of the scope. According to another aspect of the invention, the coil 12 and endoscope 3 are detached from one another along a substantial length of the coil, preferably being attached only at the distal ends 2, 16 of the endoscope 3 and actuation device 20.

According to a preferred embodiment, the coil 12 or the pull wire 18, or both are provided with an electrical coupling 34, 36, respectively for coupling to a source of cautery current. Those skilled in the art will appreciate that when two electrical couplings are provided, the pull wire 18 will be provided with insulation so that it does not electrically contact the coil 12. Alternatively, two electrically insulated pull wires may be mechanically coupled to the spool, but electrically coupled to different poles. It will also be appreciated that in either bipolar configuration, the jaws 26, 28 will be electrically insulated from each other. Certain techniques for providing electrical bipolar couplings are disclosed, e.g., in U.S. Pat. No. 5,395,369 to McBrayer et al., the complete disclosure of which is hereby incorporated herein by reference.

The actuation device 20 is substantially the same as used in many conventional endoscopic biopsy forceps. It includes a shaft 38 having a distal throughbore 40, a slot 42 in communication with the throughbore 40 and a proximal thumb ring 44. A spool 46 having a cross member 48 is disposed over the slot 42. The proximal end 14 of the coil 12 is coupled to the shaft 38 and the proximal end 22 of the pull wire 18 is coupled to the cross member 48 of the spool.

According to another aspect of the invention, the jaws 26, 28 are "open" shapes (e.g. U-shaped, semi-circular, horse shoe shaped). That is, the jaws are defined by a rim but substantially no jaw cup. Thus, the jaws do not obstruct the optical elements or lumina 4-7 at the distal end 2 of the endoscope 3.

Figure 2:
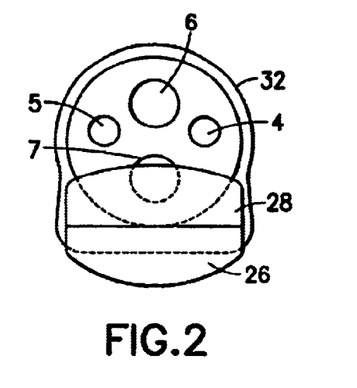
FIG. 2 is a schematic distal end view of the apparatus of FIG. 1 with the jaws closed.
Figure 3:
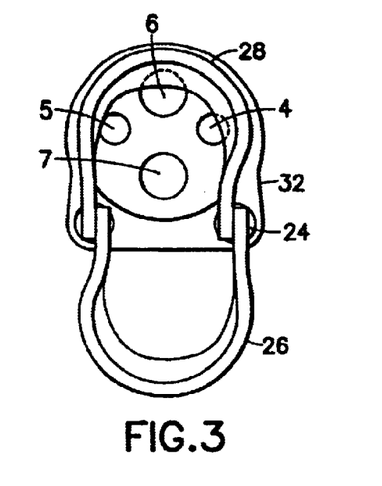
FIG. 3 is a view similar to FIG. 2 with the jaws opened.
Figure 4:
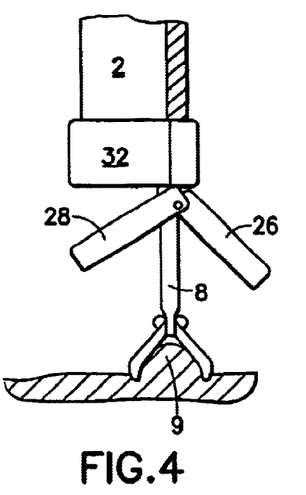
FIG. 4 is a schematic broken side elevation view of the apparatus of FIG. 1 with the jaws opened and a grasper extended from the endoscope grasping ulcerous tissue.
Figure 5:
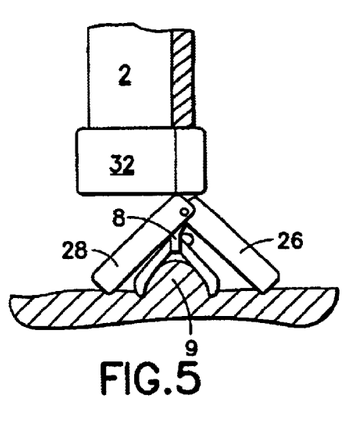
FIG. 5 is a view similar to FIG. 4 with the grasped tissue drawn into the jaws.
Figure 6:
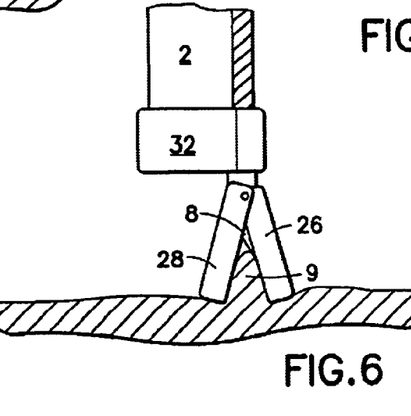
FIG. 6 is a view similar to FIG. 5 with the jaws closed around the tissue.

Turning now to FIGS. 2–6, according to one of the methods of the invention, after the clevis has been attached to the distal end of the endoscope, the jaws 26, 28 are closed as shown in FIG. 2 by activation of the actuation device 20. In the closed position, the optical elements 4, 5 of the endoscope are not obstructed by the jaws 26, 28. After the endoscope is delivered to the surgical site with the aid of the optical lumina, the jaws 26, 28 are opened as shown in FIG. 3. In the opened position shown in FIG. 3, neither the optical elements nor the lumina (including the working channel 7) of the endoscope are obstructed. As shown in FIG. 4, with the jaws open, a grasping instrument 8 such as a forceps, a biopsy forceps, a snare, a suction device, etc., is extended through the working channel 7, through an opening in the jaw 28 and/or into a space between the opened jaws 26, 28. The grasper is then actuated to grasp or retain the tissue 9 (e.g., by actuating jaws or suction), and the grasper is then partially withdrawn and/or the distal end of the endoscope is moved closer to the tissue as shown in FIG. 5 to pull the tissue between the opened jaws 26, 28. Once the tissue is between the jaws of the bipolar apparatus 10, the jaws are closed as shown in FIG. 6. According to one aspect of the invention, cauterizing energy is delivered to the jaws 26, 28 when the jaws are in the position shown in FIG. 6 to cauterize the tissue therebetween. The procedure may be repeated for treatment of other tissue in the vicinity before the apparatus is withdrawn with the endoscope.

Figure 7:
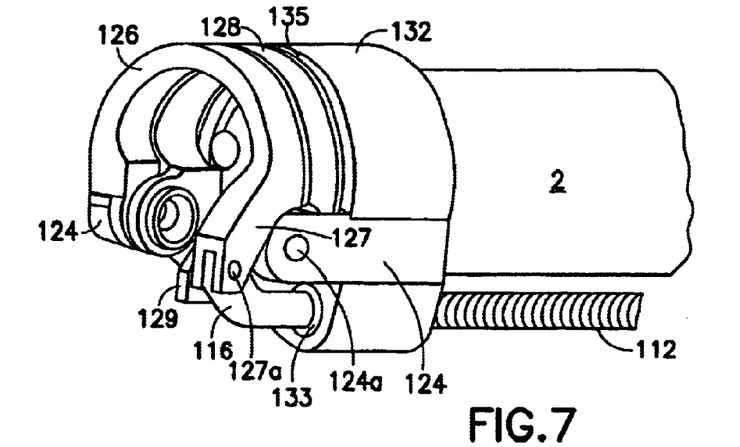
FIG. 7 is a schematic broken perspective view of a presently preferred embodiment of the jaw assembly of the invention with the jaws in a first closed position.
Figure 7A:
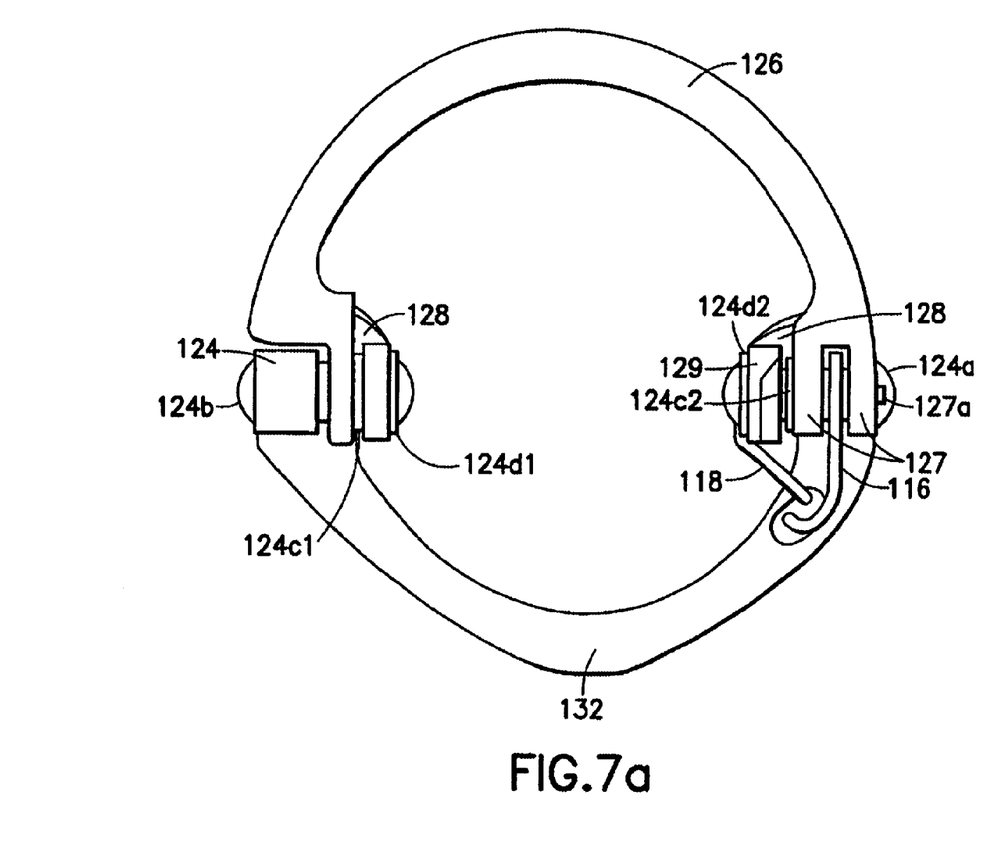
FIG. 7a is a schematic distal end view of the presently preferred embodiment with the jaws in the closed position.
Figure 8:
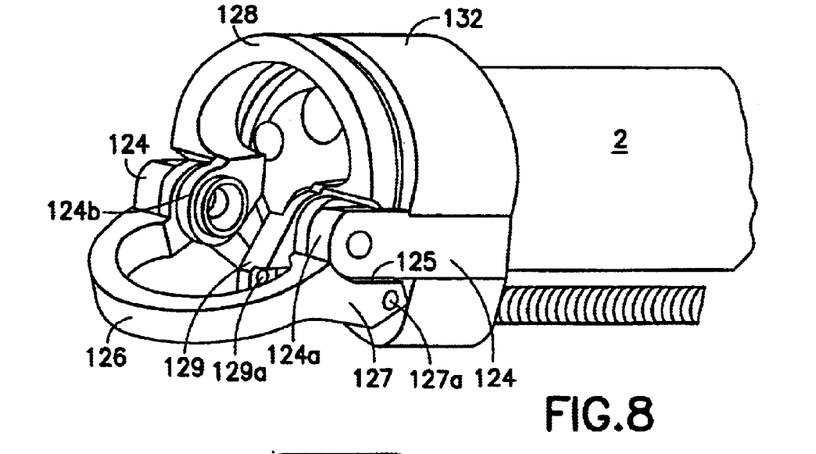
FIG. 8 is a view similar to FIG. 7 with the jaws in an opened position.
Figure 9:
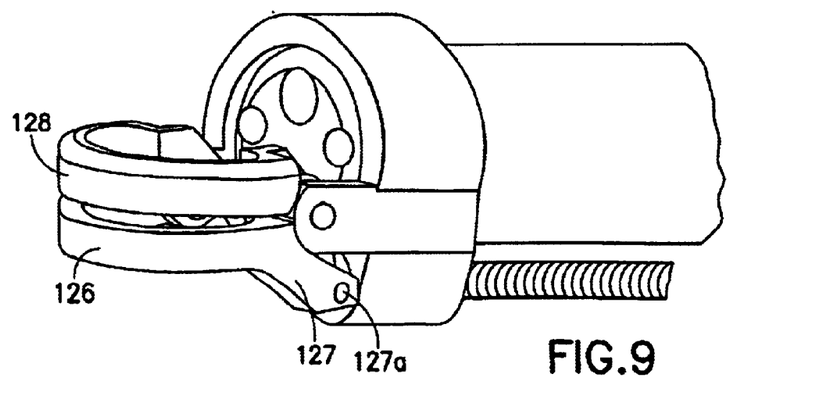
FIG. 9 is a view similar to FIG. 8 with the jaws in the second closed position.

Referring now to FIGS. 7, 7a, 8, and 9, a second embodiment of the invention is disclosed which is substantially similar to the first embodiment but for the configuration of the clevis and the jaws (i.e., the proximal actuation mechanism is as shown in FIG. 1). In this embodiment, the clevis means 124 includes an upper ring portion 132 for coupling to the distal end 2 of an endoscope. The upper portion 132 may have an inner diameter which is substantially the same size as the outer diameter of the endoscope and cemented, press fit, taped, banded, or otherwise affixed to the distal end of the endoscope. Alternatively, the upper ring portion may be sized to slide over the distal end of the endoscope. The clevis means 124 also includes a lower side throughbore 133 which is dimensioned to allow the distal end of the coil to move therethrough. Jaws 126, 128 are rotatably coupled to pivot pins 124a, 124b of the clevis 124. The jaws are preferably substantially semi-circular in shape as shown and are electrically isolated from each other by insulating washers 124c1, 124c2, 124d1, 124d2. It should be mentioned that the clevis element, including the upper ring is preferably non-conductive. The distal jaw 126 is provided with a rotator arm 127 to which the distal end of the coil is coupled at pivot pin 127a. The coil 112 actually has a rigid extension 116 at its distal end with a side opening which allows the pull wire 118 to make a 90° turn proximally of the distal end of the coil extension. The distal end of the rigid extension is coupled to the pivot pin 127a. The proximal jaw 128 is provided with a rotator arm 129 to which the distal end of the pull wire 118 is coupled at hole 129a. FIG. 7 illustrates the jaws in a first closed position. FIG. 8 shows the jaws in an open position. FIG. 9 shows the jaws in a second closed position. As shown in the Figures, the clevis means 124 is provided with a stop 125 which engages the moment arm 127 when the jaws are in the open position shown in FIG. 8 and prevents further forward movement of the jaw 126. Similarly, the upper ring 132 has a distal face 135 which prevents backward movement of the jaw 128 beyond the position shown in FIGS. 7 and 8. According to this embodiment of the invention, the distance between the pivot pin 127a and the pivot pin 124a is slightly longer than the distance between the hole 129a and the pivot pin 124a, giving the rotator arm 127 a longer moment than the rotator arm 129.

As mentioned above, the jaws 126, 128 are coupled via the coil and pull wire respectively to an actuator such as the actuation device 20 in FIG. 1. It should be intuitively clear that when the spool 46 of the actuator 20, which is attached to the pull wire, is moved distally, the distal end of the pull wire moves distally relative to the distal end of the coil. However, because movement of the pull wire cannot effect rotation of the jaw 28 as it is stopped against the face of the ring 132, the coil is effectively pulled in the proximal direction relative to the clevis means 124, thereby causing the jaw 126 to rotate about the pins 124a, 124b which constitutes the rotation axis for both jaws. This results in the jaws assuming the position shown in FIG. 8 where the rotator arms 127 and 129 are as far apart as they can be because further movement of the jaws 126, 128 is limited by the stop 125 and the distal face 135. When the spool is moved proximally, it urges proximal movement of the pull wire and distal movement of the coil. From the position of the jaws shown in FIG. 8, proximal movement of the spool will move the pull wire proximally causing the jaw 128 to move toward the jaw 126. Jaw 126, on the other hand, will only move slightly because it is impeded by the tissue it is grabbing. Thus, when the spool is moved proximally, the jaws will assume the position shown in FIG. 9 with the tissue (not shown) therebetween for cauterization. Further proximal movement of the spool would have no effect on the jaws but for the longer moment of rotator arm 127 as compared to rotator arm 129. Further proximal movement of the spool urges further proximal movement of the pull wire. However, because the pull wire is now in a most proximal position, stopped by the jaws being closed, a relative proximal movement is effected only by distal movement of the coil relative to the clevis means. The longer moment arm of the jaw 126, makes the distal movement of the coil possible. This additional movement of the coil causes the jaws to rotate about the pivots and move from the position shown in FIG. 9 to the initial closed position shown in FIG. 7. In the closed position in FIG. 7, the jaws are substantially perpendicular to the longitudinal axis of the endoscope and do not substantially block the optics or the working channel of the endoscope.

As with the first embodiment, it will be appreciated that cautery current is applied to one or both of the end effectors (jaws 126, 128) via the pull wire and/or coil. Where bipolar cautery is desired, the end effectors are preferably electrically insulated relative to each other, and each end effector is provided with a different pole.

According to another aspect of the invention, bipolar cauterization of the surgical site may be achieved by providing the grasping device which extends through the endoscope with one pole, and by providing one or both jaws of the external tool with a second electrical pole.

It will be appreciated that the disclosed invention provides several inventive aspects. One particular aspect is providing a pair of end effectors on the outside of the distal end of the endoscope, in which one end effector is rotatable or otherwise movable relative to the second end effector, and also provide another instrument through the lumen of the endoscope, particularly where such other instrument also has a pair of end effectors.

With respect to this inventive aspect, it is appreciated that the other end effectors may be coupled to the outside of the distal end of the endoscope in accord with previously described or similar coupling structure (i.e., be "on-scope) in place of the bipolar jaws described. This concept will now be described by way of example with respect to several additional end effector assemblies.

Figure 10:
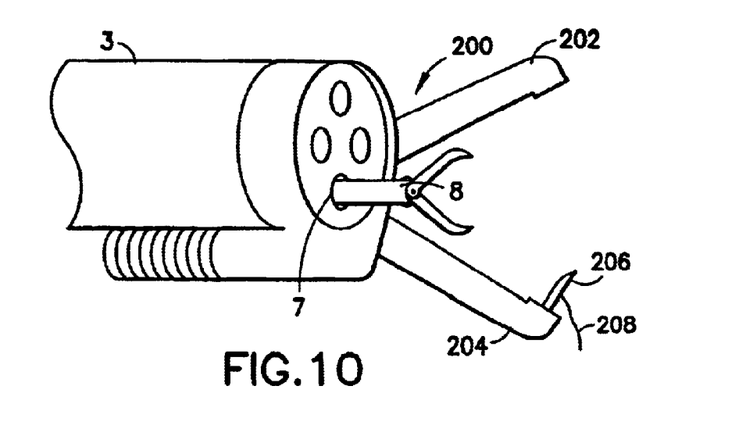
FIG. 10 is a schematic broken side elevation view of a third embodiment of the invention.

Referring first to FIG. 10, the on-scope end effector assembly is a needle passer system 200 having two arms 202, 204 each of which is adapted to alternately hold a needle 206 having suture material 208. The system automatically passes the needle 206 back and forth between the arms 202, 204 to form stitches of the suture material in a tissue between the arms. The actuation and operation of the arms to automatically pass a needle is described in U.S. Pat. No. 5,814,054 to Kortenbach, et al. hereby incorporated by reference herein in its entirety. A grasper 8 extending through a lumen 7 of the endoscope 3 may then be used to pull tissue between the arms 202, 204 of the needle passer system 200, and the needle passer system 200 is then concurrently operated to pass the needle 206 and suture material 208 back and forth through the tissue.

Figure 11:
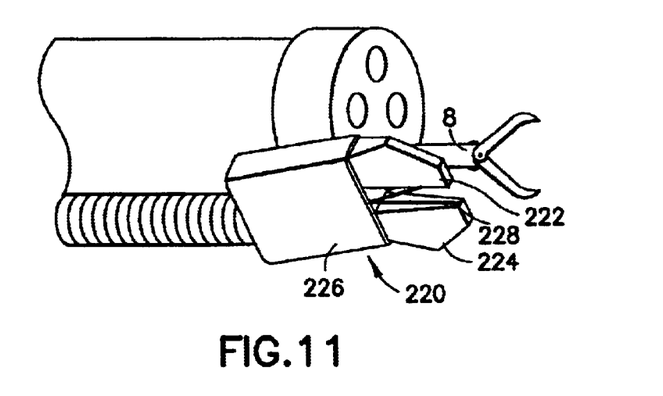
FIG. 11 is a schematic broken side elevation view of a fourth embodiment of the invention.

Turning now to FIG. 11, the on-scope end effector assembly is a multi-fire clip applier 220 having two arms 222, 224 at least one of which can be moved relative to the other, and a chamber 226 storing a plurality of clips 228. The clips 228 can be advanced single file from the chamber into a space between the arms. The through-the-scope grasper 8 may be used to pull tissue between the arms 222, 224 of the clip applier, at least one of the arms is moved toward the other, and the clip applier may be actuated to fire one or more clips into or about the tissue. Multi-fire clip appliers are described in U.S. Pat. Nos. 5,993,465 to Shipp et al., 6,099,537 to Sugai et al., 5,681,330 to Hughett et al., and also in co-owned U.S. Ser. No. 10/010,906, filed Dec. 6, 2001, all of which are hereby incorporated by reference herein in their entireties.

Figure 12:
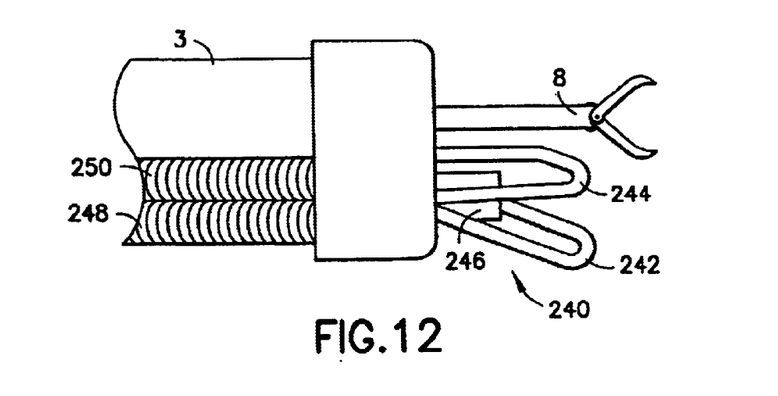
FIG. 12 is a schematic broken side elevation view of a fifth embodiment of the invention.

Referring now to FIG. 12, the on-scope end effector assembly is a tripolar hemostat/cutter 240 including two U-shaped bars 242, 244 of a common pole, and a centralized cutter element 246 of the opposite pole. The bars 242, 244 are adapted to be moved relative to the cutter 246, and energy travels from the cutter to the bars (or vice versa) to seal tissue between the bars. Two insulated coils 248, 250 (or other tubular members) running along the outside of the endoscope 3 are adapted to insulatively extend positive and negative leads (not shown) from a power source (not shown) to the bars 242, 244 and cutter 246. The operation of a tripolar cutter is described in detail in U.S. Pat. No. 5,951,545 to Schilling et al., which is hereby incorporated by reference herein in its entirety.

Figure 13:
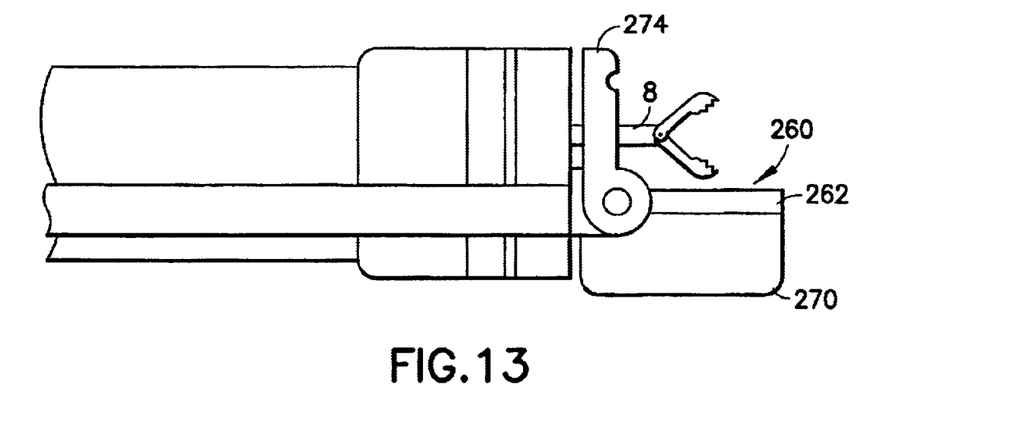
FIG. 13 is a schematic broken side elevation view of a sixth embodiment of the invention.
Figure 14:
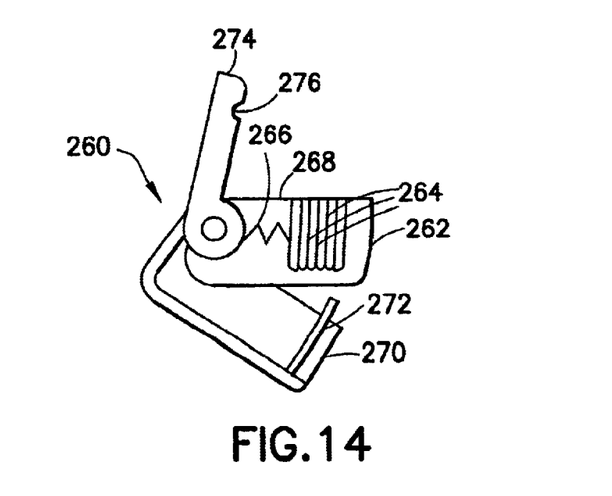
FIG. 14 is a schematic broken side elevation view in partial section of a portion of the sixth embodiment of the invention.

Turning now to FIGS. 13 and 14, the on-scope end effector is a stapler 260 having a central chamber 262 which stores staples 264 and advances the staples, preferably via a spring 266, into a launch position 268. The stapler also includes a first arm 270 having a pusher 272, and a second arm 274 having an anvil 276. The grasper 8 pulls tissue between the chamber 262 and the second arm 274. The first and second arms 270, 274 are then rotated relative to the chamber 262 such that the pusher 272 pushes a staple 264 from the launch location 268 through the tissue until the staple 264 plastically deforms against the anvil 276 to hold the staple in the tissue. Exemplar stapler mechanisms are described in detail in U.S. Pat. Nos. 6,312,437 to Kortenbach, 6,119,913 to Adams et al., 5,829,662 to Allen et al., 5,817,109 to McGarry et al., 5,779,132 to Knodel et al., 5,497,933 to DeFonzo et al., and 5,392,978 to Velez, which are hereby incorporated by reference herein in their entireties.

Referring now to FIGS. 15 through 20, the on-scope end effector is a hemoclip assembly 280. The hemoclip assembly includes a preferably double-wide hemoclip having a pair of U-shaped jaws 282, 283 joined by a proximal bridging portion 284, and a pair of closing tubes 285, 286 also joined by a bridge 287. Each half of the double-wide hemoclip preferably has a shape similar to a clip shown and described in detail in U.S. Pat. No. 6,099,537 to Sugai et al, which is hereby incorporated by reference herein in its entirety. The hemoclip 280 may be rotated from a first position (FIG. 15) relative to the closing tubes 285, 286 in which a line $L_1$ extending between both jaws 282, 283 is oriented substantially perpendicular to the axis A of the scope 3, to a second position (FIG. 16) relative to the closing tubes in which a line $L_2$ extending between both jaws is oriented substantially parallel to the axis A of the scope 3. In the first position, the U-shape of the jaws permit visualization by the scope through the jaws. The hemoclip 280 is moved relative to the end of the scope 3 in a manner similar to the movement of the cautery jaws 126, 128 of the second embodiment of the invention using a combination of a pull wire 118 and a coil 112. The pull wire 118 is coupled to the bridge portion 284 of the hemoclip 280 via a frangible link 288.

Figure 15:
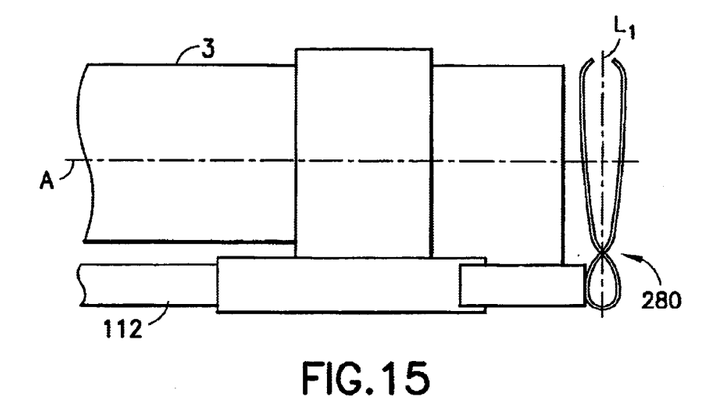
FIG. 15 is a schematic broken side elevation view of a seventh embodiment of the invention, shown with an attached end effector in a first orientation.
Figure 16:
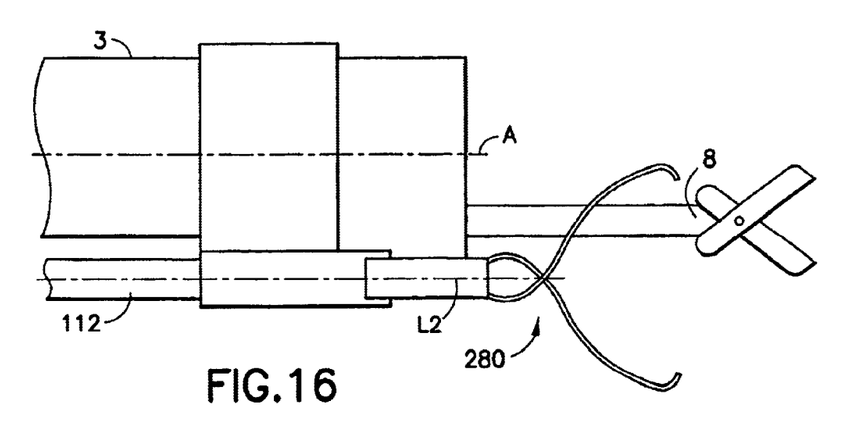
FIG. 16 is a schematic broken side elevation view of the seventh embodiment of the invention, shown with an attached end effector in a second orientation.
Figure 17:
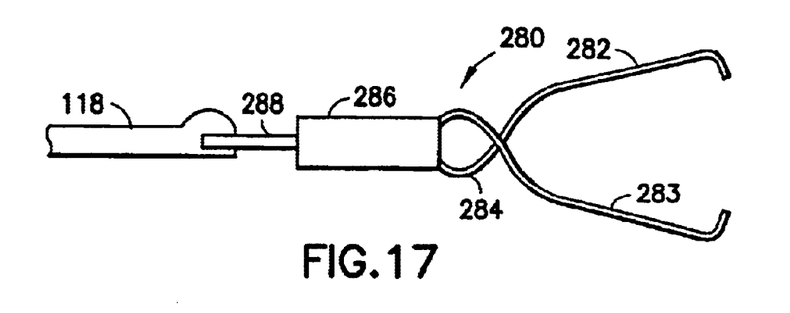
FIG. 17 is a schematic broken side elevation view of a portion of the seventh embodiment of the invention.
Figure 18:
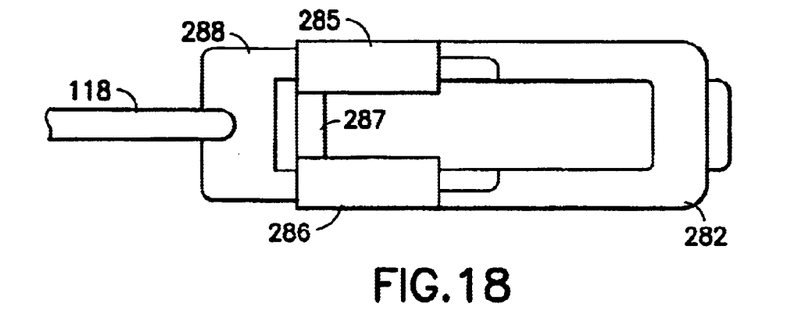
FIG. 18 is a schematic broken top view of a portion of the seventh embodiment of the invention.
Figure 19:
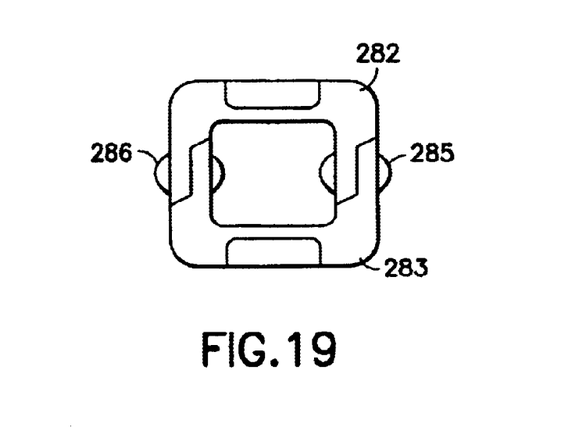
FIG. 19 is a schematic distal end view of a portion of the seventh embodiment of the invention.
Figure 20:
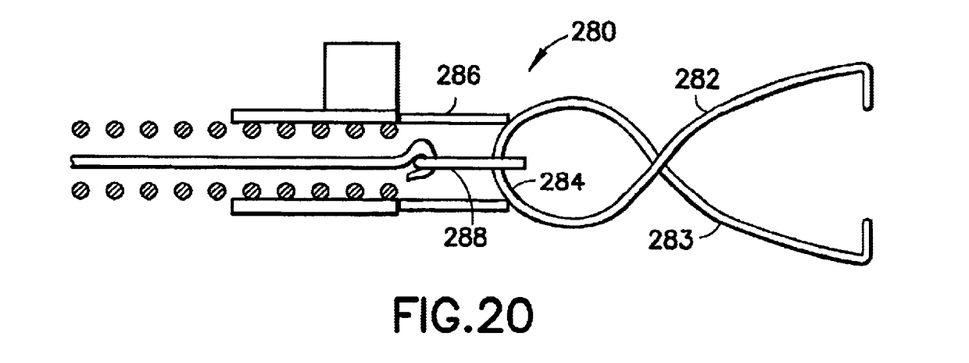
FIG. 20 is a schematic broken side elevation view in partial section of the seventh embodiment of the invention.

According to one method of using the hemoclip, the endoscope is manipulated relatively close to tissue and the hemoclip is moved from the first position to the second position (FIGS. 15 and 16). A grasper 8 is then passed through the working channel of the endoscope 3 to grasp tissue and pull it between the jaws 282, 283 of the hemoclip 280. The hemoclip is then closed about the tissue by pulling the pull wire 118 relative to the coil 112 such that proximal portions of the jaws 282, 283 are pulled into the tubes 285, 286 and effect closure of the jaws about the tissue. The grasper 8 is operated to release the tissue, and the pull wire 118 of the hemoclip assembly 280 is then pulled further to break the frangible link 288 such that the hemoclip separates from the endoscope 3 and remains on the tissue.

Figure 21:
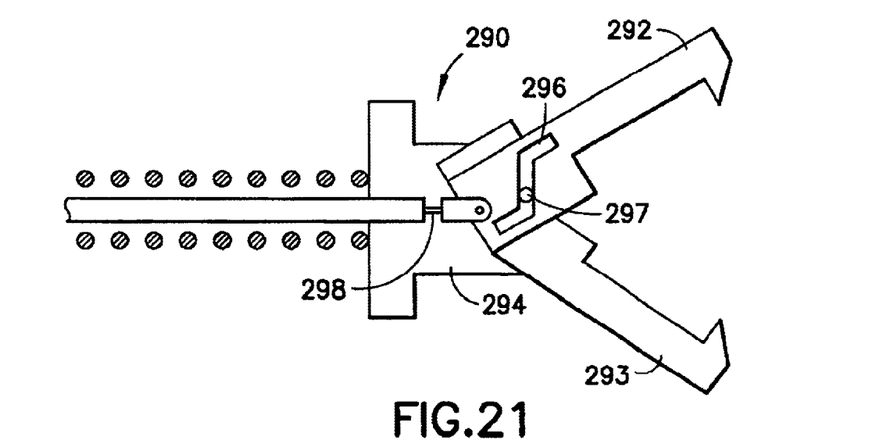
FIG. 21 is a schematic broken side elevation view in partial section of an eighth embodiment of the invention.

Turning now to FIG. 21, another hemoclip 290 is shown having a relatively different mechanism for closing the jaws 292, 293. The jaws 292, 293 are rotatably coupled about a clevis 294 and include a locking mechanism (e.g., a slotted locking cam 296 movable over a pivot 297) which can maintain the jaws 292, 293 in a closed position. Alternatively, teeth (not shown) can be used to lock the jaws together. The jaws can then be released by breaking a frangible link 298.

Moreover, while various on-scope end effectors may be used at the distal end of the endoscope, it will also be appreciated that instruments other than graspers may be used through the endoscope, preferably in a manner which cooperates with the on-scope end effector.

Figure 22:
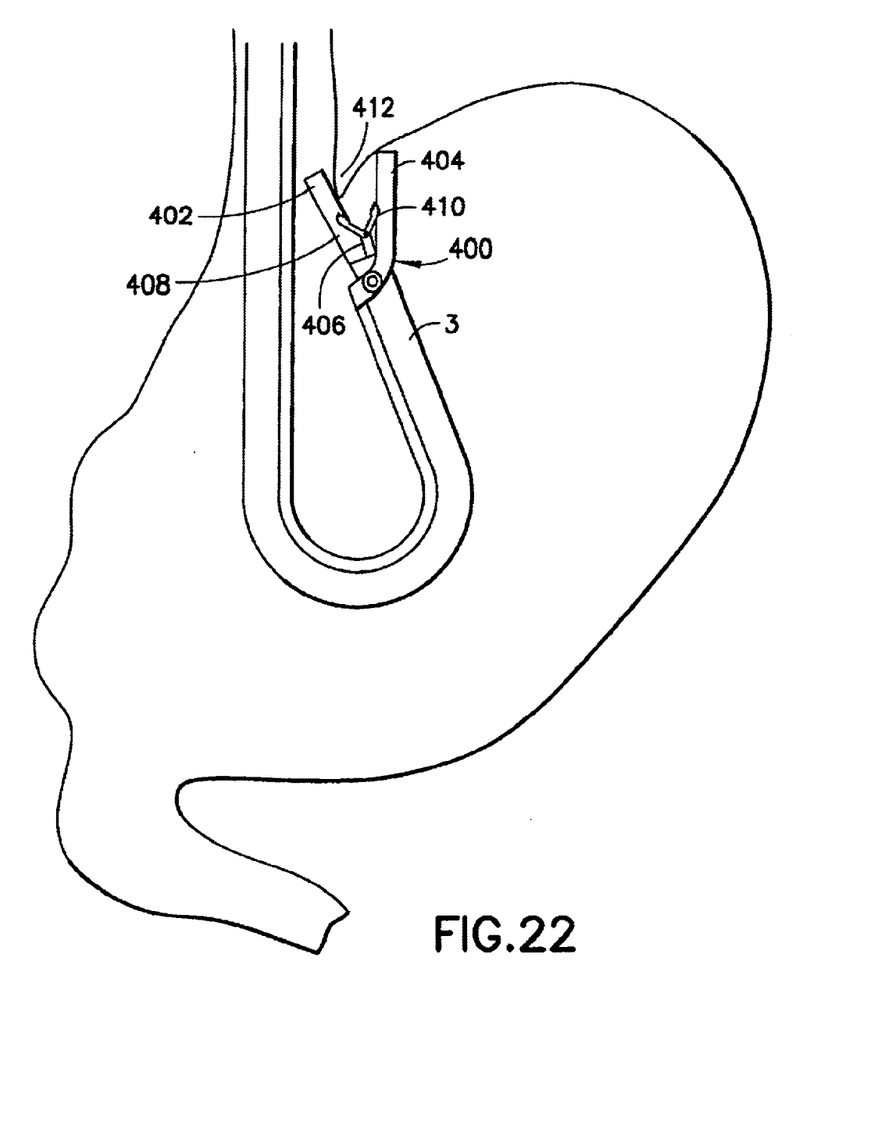
FIG. 22 is a schematic broken partially transparent view of a ninth embodiment of the invention in a first use.

For example, turning now to FIG. 22, the endoscope 3 is provided with an on-scope grasper assembly 400 including jaws 402, 404 such as described above with respect to the first and second embodiments of the invention, though not necessarily requiring cautery capability, and the through-scope instrument is a clip applier 406 having first and second jaws 408, 410 adapted to close about tissue and apply a clip (not shown) over and/or through the tissue. Such a clip applier is described in detail in co-owned U.S. Ser. No. 10/010,906 filed Dec. 6, 2001, which is hereby incorporated by reference herein in its entirety. In operation, the grasper jaws 402, 404 may grab and hold tissue, e.g., the fundus 412 of the stomach or esophageal tissue, while the jaws 408, 410 of the clip applier 406 surround a portion of the tissue held by the grasper jaws and apply a clip thereover.

From the above examples, it will be appreciated that the invention can broadly be related to a combination of on-scope and through-scope instruments in which each of the on-scope and through-scope instrument has an end effector.

There have been described and illustrated herein several embodiments of a surgical instrument for use with an endoscope. While particular embodiments of the invention have been described, it is not intended that the invention be limited thereto, as it is intended that the invention be as broad in scope as the art will allow and that the specification be read likewise. Thus, while the illustrative embodiments incorporate most or all of the inventive features of the invention, it will be appreciated as described above that some of the inventive features may be applied alone or in combinations other than those of the disclosed embodiments. In addition, it will be appreciated that while particular embodiments have been shown, other embodiments of the invention can be utilized. For example, rather than providing a tool adjacent and clipped to the endoscope which utilizes a coil and a pull wire, the coil could be replaced with a tube (e.g., a hypotube), and/or the pull wire could be replaced with a rod, or a cable (metallic or otherwise). In each case, the extent of flexibility of tube and rod can be dependent upon the application in which the endoscope is used. Also, rather than providing a tool where the jaws rotate about pivot pins or axis, one jaw could be caused to rotate, pivot, or otherwise open relative to the other jaw, e.g., using an arcuate coupling such as disclosed in U.S. Pat. No. 5,389,104 to Hahnen et al., which is hereby incorporated by reference herein in its entirety. For purposes herein, all such rotation or pivoting is called "rotation". Furthermore, while external on-scope coupling structure attaching the end effector about the outside of the scope is preferred, it is appreciated that such attachment may additionally or alternatively be within a suction and/or irrigation lumen, or one working channel of a multichannel endoscope; i.e., a fully or partially internal "on-scope" coupling. Moreover, it is recognized from the above that other effecting elements which rotate relative to each other or move in a non-longitudinal manner (i.e. where effecting elements move linear toward each other in a direction other than along the axis of the endoscope) relative to each other can be used. It will therefore be appreciated by those skilled in the art that yet other modifications could be made to the provided invention without deviating from its spirit and scope.

We claim:

1. A surgical system for performing surgery on tissue, comprising:
   a) an endoscope having a lumen and a distal end;
   b) a surgical tool coupled to said distal end of said endoscope in a longitudinally fixed manner, said surgical tool including,
      i) a first end effector, and
      ii) actuation means for actuating said first end effector; and
   c) an instrument extendable through said lumen of said endoscope, wherein said instrument includes a second end effector axially extendable through and beyond said first end effector and adapted to axially pull the tissue between said first end effector for manipulation of the tissue by said first end effector.

2. A surgical system according to claim 1, wherein:
said actuation means actuates said first end effector without passing through the lumen of the endoscope.

3. A surgical system according to claim 1, wherein:
said second end effector includes two effecting elements, at least one of which is movable relative to the other.

4. A surgical system according to claim 1, wherein:
said instrument includes one of a forceps, a biopsy forceps, a snare, and a suction device.

5. A surgical system according to claim 1, wherein:
said surgical tool is coupled externally about said distal end of said endoscope.

6. A surgical system according to claim 5, wherein:
said surgical tool is coupled to said distal end of said endoscope with a collar.

7. A surgical system according to claim 1, wherein:
said first end effector includes two effecting elements, at least one of which is movable relative to the other.

8. A surgical system according to claim 7, wherein:
said two end effecting elements of said first end effector are each movable relative to the other.

9. A surgical system according to claim 7, wherein:
at least one of said effecting elements is movable in a non-longitudinal direction relative to the other.

10. A method of performing a surgical procedure, comprising:
    a) providing an endoscope having a lumen, a longitudinal axis, a distal end, and a surgical tool coupled to said distal end, said surgical tool including a first end effector including two effecting elements, at least one of which is movable relative to the other;
    b) opening said two effecting elements of said first end effector to provide a passage therebetween, said passage being parallel to said longitudinal axis;
    c) extending an endoscopic instrument having a second end effector through said lumen until said second end effector extends through said passage between said effecting elements;
    d) grasping a body tissue with said endoscopic instrument;
    e) pulling said body tissue axially between said effecting elements of said first end effector of said surgical tool; and
    f) manipulating the body tissue with said effecting elements of said first end effector of said surgical tool.

11. A method according to claim 10, wherein:
said surgical tool includes a control element extending from a proximal portion of said endoscope to said end effector of said surgical tool, and said control element does not pass through said lumen of said endoscope, said control element actuated by said operating said effecting elements of said first end effector of said surgical tool.

12. A method according to claim 10, wherein:
said surgical tool further includes a tubular member about said control member, said tubular member being coupled to said endoscope at a distal end of said endoscope and being detached from said endoscope along a portion proximal to said distal end of said endoscope.

13. A method according to claim 10, wherein:
said manipulating of said tissue includes at least one of clamping, cutting, cauterizing, stapling, clipping, and hemostasis application.

14. A method according to claim 10, wherein:
said opening said first end effector includes rotating at least one effecting element relative to the other end effector.

15. A method according to claim 10, wherein:
said opening said first end effector includes moving at least one effecting element in a non-longitudinal direction relative to the other end effector.

* * * * *